United States Patent
Park Choo et al.

(10) Patent No.: US 7,329,682 B2
(45) Date of Patent: Feb. 12, 2008

(54) METHOD FOR INHIBITING 5-LIPOXYGENASE USING A BENZOXAZOLE DERIVATIVE

(75) Inventors: Hea Young Park Choo, Seoul (KR); Hyeun Wook Chang, Daegu (KR); Ju Hee Yoon, Seoul (KR); Hye Kyung Ju, Daegu (KR)

(73) Assignee: EWHA University-Industry Collaboration Foundation (KR)

( * ) Notice: Subject to any disclaimer, the term of this patent is extended or adjusted under 35 U.S.C. 154(b) by 347 days.

(21) Appl. No.: 10/789,725

(22) Filed: Feb. 27, 2004

(65) Prior Publication Data

US 2004/0198768 A1   Oct. 7, 2004

(30) Foreign Application Priority Data

Apr. 3, 2003 (KR) ............... 10-2003-0021055
Jul. 11, 2003 (KR) ............... 10-2003-0047104

(51) Int. Cl.
*A61K 31/423* (2006.01)
(52) U.S. Cl. .................................. 514/377
(58) Field of Classification Search .............. None
See application file for complete search history.

(56) References Cited

OTHER PUBLICATIONS

Chang et al., Chemistry Letters, pp. 1291-1294 (1986).*
Elmina et al., Antimicrobial Agents and Chemotherapy, 19(1), p. 29-32 (Jan. 1981).*
Henderson, W., Annals of Internal Medicine, 121(9), (Nov. 1, 1994), pp. 684-697.*

* cited by examiner

*Primary Examiner*—Phyllis G. Spivack
(74) *Attorney, Agent, or Firm*—Anderson Kill & Olick, PC

(57) ABSTRACT

A benzoxazole derivative is disclosed for inhibiting 5-lipoxygenase.

2 Claims, No Drawings

METHOD FOR INHIBITING 5-LIPOXYGENASE USING A BENZOXAZOLE DERIVATIVE

FIELD OF THE INVENTION

The present invention relates to a method for inhibiting 5-lipoxygenase in a subject using a benzoxazole derivative or an analogue thereof.

BACKGROUND OF THE INVENTION

Leukotriene is derived from arachidonic acid by a lipoxygenase pathway, e.g., leukotriene $C_4$ ($LTC_4$) is synthesized from arachidonic acid by the actions of 5-lipoxygenase and $LTC_4$ synthase. $LTC_4$ has long been recognized as a potent mediator of inflammation involved in diseases such as asthma, cystic fibrosis, acute/chronic bronchitis, gout, rheumatic arthritis, arthritis, allergic rhinitis, skin disorder such as psoriasis, and inflammatory bowel disease. Further, leukotriene is known to be related to various cardiopulmonary diseases including sepsis, cardiac myoischemia, cardiac anaphylaxis, cerebrovascular convulsion and ischemia. Accordingly, a compound capable of selectively suppressing 5-lipoxygenase can be effectively used in treating the above diseases.

There have been reported various compounds suppressing 5-lipoxygenase, e.g., compounds having a hydroxyurea, hydroxamate, aryl alcohol or carboxylic acid Moiety. However, these compounds generally suffer from the multiple problems of toxicity such as formation of methemoglobin and poor bioavailability.

Accordingly, there has been a need to develop a drug capable of suppressing leukotriene-related diseases such as asthma and inflammation diseases by effectively inhibiting 5-lipoxygenase. The present inventors have found that benzoxazole derivatives are effective 5-lipoxygenase inhibitors.

Benzoxazole moieties, which are known to act as antibiotics, antitumors and fluorescent whitening agents, have been synthesized by a number of methods. For instance, Anitha Hari et al. reported a method for synthesizing benzoxazole derivatives using 2-aminophenol and an aldehyde as starting materials (*J. Org. Chem.* 66 pp.991-996(2001)). Further, for the cyclization of thiourea, an intermediate of benzoxazole derivative, Haruo Ogura et al. used nickel peroxide as an oxidizing agent (*J. Soc. Chem. Lett.* pp.1291-1294(1986)), while Hae Sung Chang et al. employed potassium superoxide (*Chem. Pharm. Bull* 29(6) pp.1518-1524 (1981)). However, these methods suffer from the problem of vigorous reaction conditions due to the use of the oxidizing agents.

Accordingly, it is desirable to develop a preparation method thereof which can be carried out in mild conditions.

SUMMARY OF THE INVENTION

It is an object of the present invention to provide a method for inhibiting 5-lipoxygenase in a subject using a benzoxazole derivative or an analogue thereof.

It is another object of the present invention to provide an improved method for preparing said benzoxazole derivative.

In accordance with one aspect of the present invention, there is provided a method for inhibiting 5-lipoxygenase in a subject, comprising administering a compound of formula (I) or a pharmaceutically acceptable salt thereof to the subject in an amount effective for the inhibition of 5-lipoxygenase:

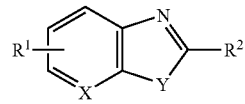
(I)

wherein

X is CH or N;

Y is S or O;

$R^1$ is H, OH, halogen, $C_{1-6}$ alkyl, nitro, cyano, amino, di-$C_{1-6}$ alkylamino, $C_{1-6}$ alkoxy, $C_{1-6}$ hydroxyalky or $C_{1-6}$ alkylcarbonyl; and $R^2$ is

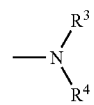
(i)

wherein $R^3$ is H or $C_{1-6}$ alkyl;

$R^4$ is

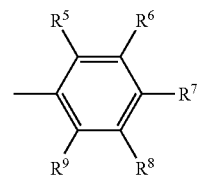

wherein $R^5$, $R^6$, $R^7$, $R^8$ and $R^9$ are independently H, OH, halogen, $C_{1-6}$ alkyl, $C_{1-6}$ haloalkyl, nitro, cyano. aminl, di-$C_{1-6}$ alkylamino, mercapto, $C_{1-6}$ mercaptoalky, halogen-substituted $C_{1-6}$ mercaptoalkyl, phenylazo, $C_{1-6}$ alkylphenylazo, $C_{1-6}$ alkylcarbonyl, $C_{1\ 6}$ alkoxy or $C_{1-6}$,

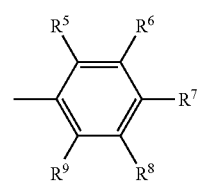
(ii)

wherein $R^5$, $R^6$, $R^7$, $R^8$ and $R^9$ are as defined in (i), (iii)

wherein $R^{10}$ is H or $C_{1-6}$ alkyl,

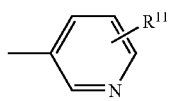

wherein $R^{11}$ is H, $C_{1-6}$ alkyl, halogen, mercapto or $C_{1-6}$ mercaptoalkyl, or

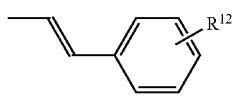

wherein $R^{12}$ is H, OH, halogen, $C_{1-6}$ alkyl, nitro, cyano, amino, di-$C_{1-6}$ alkylamino, $C_{1-6}$ alkylcarbonyl, $C_{1-6}$ alkoxy or $C_{1-6}$ hydroxyalkyl.

In accordance with another aspect of the present invention, there is provided a method for preparing the compound of formula (I).

DETAILED DESCRIPTION OF THE INVENTION

Preferred compounds of formula (I) used in the present invention are those wherein $R^2$ is

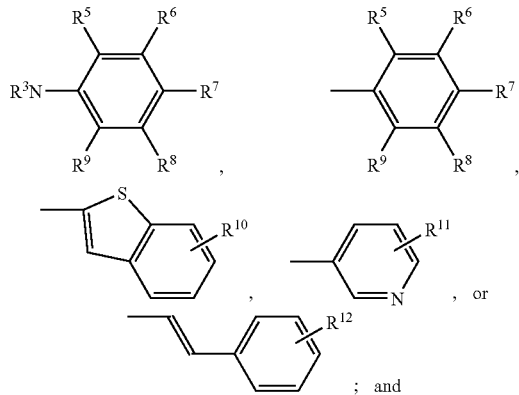

$R^3$, $R^5$, $R^7$, $R^8$, $R^9$, $R^{10}$, $R^{11}$ and $R^{12}$ are as defined in formula (I).

In the inventive method for inhibiting 5-lipoxygenase, the compound of formula (I) can be administered to a patient in the form of a pharmaceutical composition comprising the compound or a pharmaceutically acceptable salt thereof.

Exemplary pharmaceutically acceptable salts that may be used in the present invention include therapeutically active, non-toxic acid-addition salts of the compound of formula (I).

These salts can be prepared by treating the compound of formula (I) with a suitable acid, for example, hydrochloric acid, hydrobromic acid, sulfuric acid, nitric acid, phosphoric acid, acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid and p-toluenesulfonic acid.

Due to its 5-lipoxygenase inhibiting activity, the compound of formula (I) is an effective agent for preventing or treating a leukotriene-related disease in human, e.g., asthma, pertussis, psoriasis, rheumatic arthritis, arthritis, inflammatory bowel disease, cystic fibrosis, acute/chronic bronchitis, gout, sepsis, cardiac myoischemia, cardiac anaphylaxis, cerebrovascular convulsion, ischemia and allergic rhinitis.

When used for the above purposes, said compound may be administered via the oral, parenteral or topical route. The compound may be administered as is but is preferably administered in the form of a composition which is formulated with a pharmaceutically acceptable carrier and optional excipients, flavors, adjuvants, etc. in accordance with good pharmaceutical practice.

The composition may be in the form of a solid, semi-solid or liquid dosage form: such as tablet, capsule, pill, powder, suppository, solution, elixir, syrup, suspension, cream, lozenge, paste and spray. As those skilled in the art would recognize, depending on the chosen route of administration, the composition form of said 5-lipoxygenase inhibitor is determined. In general, it is preferred to use a unit dosage form of the inventive inhibitor in order to achieve an easy and accurate administration of the active compound. In general, the therapeutically effective compound of formula (I) is present in such a dosage form at a concentration level ranging from about 0.5% to about 90% by weight of the total composition: i.e., in an amount sufficient to provide the desired unit dose.

The 5-lipoxygenase inhibitor compound of formula (I) may be administered in single or multiple doses. The particular route of administration and the dosage regimen will be determined by the attending physician in keeping with the condition of the individual to be treated and said individual's response to the treatment. For oral administration, doses of from about 10 mg to about 1000 mg per day in single or multiple doses may be sufficient. For parenteral administration, doses of from about 5 mg to 800 mg per day may be used in single or multiple doses. In some instances, dosage levels below the lower limit of the aforesaid range may be more than adequate, while in other cases still larger doses may be employed without causing any harmful or deleterious side effects, provided that such higher dose levels are first divided into several smaller doses that are to be administered throughout the day.

For oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium sterate, sodium lauryl sulfate and talc are often used for tabletting. Solid compositions of a similar type may also be employed as fillers in soft and hard-filled gelatin capsules; preferred materials in this connection include lactose or milk sugar as well as high molecular weight polyethylene glycols. When aqueous suspensions and/or elixirs are desired for oral administration, the active ingredient may be combined with various sweetening or flavoring agents, colorants or dyes, and, if so desired, emulsifying and/or suspending agents as well, together with such diluents as water, ethanol, propylene glycol, glycerin and various like combinations thereof.

The present invention also provides a pharmaceutical composition in a unit dosage form for the inhibition of 5-lipoxygenase activity in a patient in need of such treatment, comprising a compound of formula (I) and one or more nontoxic pharmaceutically acceptable carriers, adjuvants or vehicles. The amount of the active ingredient that may be combined with such materials to produce a single dosage form will vary depending upon various factors, as indicated above.

A variety of materials can be used as carriers, adjuvants and vehicles in the composition of the invention, as available in the pharmaceutical art. injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol.

Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

Suppositories for rectal administration of the compound of formula (I) can be prepared by mixing the drug with a suitable nonirritating excipient such as cocoa butter and polyethylene glycols, which are solid at ordinary temperatures but liquid at body temperature and which therefore melt in the rectum and release the drug.

Additionally, it is also possible to administer the aforesaid compounds topically and this may be preferably done by way of cream, salve, jelly, paste, ointment and the like, in accordance with the standard pharmaceutical practice.

The present invention also provides an improved method for preparing the compound of formula (I).

Specifically, the representative compounds of formula (I), i.e., compounds of formula (Ia) and (Ib) can be prepared in accordance with a process shown in the following reaction scheme:

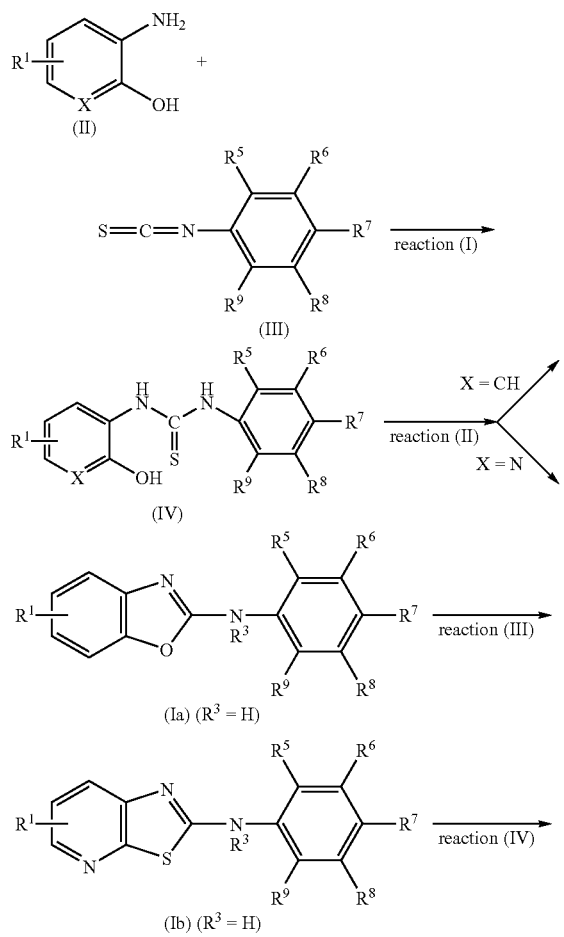

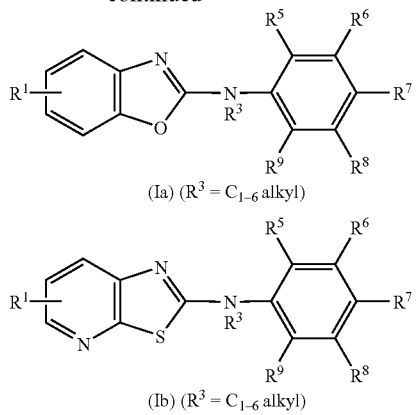

wherein $R^1$, $R^3$, $R^5$, $R^6$, $R^7$, $R^8$ and $R^9$ are as defined in formula (I).

As shown in the above reaction scheme, the compound of formula (II) is reacted with the compound of formula (III) in a suitable organic solvent to produce a thiourea intermediate of formula (IV) (reaction I).

The compound of formula (III) is preferably employed in an amount ranging from 1 to 1.5 equivalents, more preferably 1 to 1.2 equivalents, based on 1 equivalent of the compound of formula (II). reaction (I) is performed at or above room temperature, preferably at room temperature, for a period ranging from 1 to 24 hours, preferably over 12 hours. It is also possible to carry out the reaction for over 24 hours.

Preferred organic solvents that may be used in the present invention include methanol, ethanol, ether and the like, and methanol is most preferred.

The thiourea intermediate of formula (IV) is obtained as a precipitate, and the end point of the reaction (I) may be identified by thin-layer chromatography.

The resulting thiourea intermediate of formula (IV) is then cyclized by reacting with an acid to synthesize the compound of formula (Ia) ($R^3$=H) (reaction II). The acid is added in an amount sufficient to dissolve the thiourea intermediate.

The reaction (II) is performed at a temperature ranging from a room temperature to a reflux temperature, preferably, the reflux temperature, for a period ranging from 1 to 24 hours, preferably over 12 hours. It is also possible to carry out the reaction for over 24 hours.

Exemplary acids that may be used in the present invention include trifluoroacetic acid, phosphoric acid, sulfuric acid, hydrochloric acid and nitric acid; while trifluoroacetic acid and phosphoric acid are more preferred; with trifluoroacetic acid being most preferred.

After completion of the reaction, the acid is removed using any of the conventional methods to obtain a desired product. For example, when trifluoroacetic acid is used, rotaty evaporation may be used.

Furthermore, the compounds of formulae (Ia) and (Ib), wherein each $R^3$ is $C_{1-6}$ alkyl, can be prepared from the corresponding compounds wherein each $R^3$ is H, by a conventional substitution reaction process (reactions III and IV).

The following Examples are intended to further illustrate the present invention without limiting its scope.

EXAMPLE 1

Preparation of 2-phenylamino pyridinothiazole

2-Hydroxy-3-aminopyridine (70 mg, 0.64 mmol) and phenyl isothiocyanate (100 μl, 0.83 mmol) in methanol (25 ml) was stirred at room temperature for a day. The precipitate was filtered and washed with methanol to obtain N-(2-hydroxypyridino)-N'-phenyl thiourea as a yellow powder. N-(2-hydroxypyridino)-N'-phenyl thiourea(39.2 mg, 0.16 mmol) was then treated with trifluoroacetic acid (5 ml), refluxed for a day, trifluoroacetic acid was removed by rotary evaporation, and the crude product was purified by column chromatography (ethyl acetate: hexane=3: 1 v/v) to obtain the title compound as a white powder.

EXAMPLES 2 and 3

Pyridinothiazole compounds were obtained by the procedure of Example 1 using respective starting material The compounds obtained in Examples 1 to 3 and characteristic properties thereof are shown in Table 1.

TABLE 1

| Ex. | $R^6$ | $R^7$ | Data |
|---|---|---|---|
| 1 | —H | —H | mp: 162-164° C.<br>IR(KBr): 3271, 2927, 2852, 1519, 1212, 750, cm$^{-1}$.<br>$^1$H NMR(DMSO-d$_6$, 400MHz): δ9.65(s, NH), 8.23-8.22(s, 1H), 7.86-7.83(m, 3H), 7.39-7.35(t, J=12Hz, 1H), 7.33-7.32(s, 1H), 7.31(s, 1H), 7.09-7.05(t, J=12Hz, 1H). FAB/MS(m/z): 228(M$^+$+1). |
| 2 | —H | —C$_2$H$_5$ | IR(KBr): 3282, 2933, 2858, 1670, 1519, 1202, 833, 798, 720, cm$^{-1}$.<br>$^1$H NMR(acetone-d$_6$, 400MHz): δ9.58(s, NH), 8.21-8.20(s, 1H), 7.83-7.81(d, J=8Hz, 1H), 7.74-7.72(d, J=8Hz, 2H), 7.33-7.30(m, 1H), 7.23-7.21(d, J=8Hz, 2H), 2.62-2.60(d, J=8Hz, 2H), 1.21-1.18(m, 3H). FAB/MS(m/z): 256(M$^+$+1). |
| 3 | —Cl | —Cl | mp: 270-272° C.<br>IR(KBr): 3395, 2922, 2857, 1599, 1459, 1029, cm$^{-1}$. $^1$H NMR(acetone-d$_6$, 400MHz): δ10.82(s, NH), 8.35-8.34(s, 1H), 8.30-8.29(s, 1H), 7.96-7.95(s, 1H), 7.76-7.74(d, J=8Hz, 1H), 7.56-7.54(d, J=8Hz, 1H), 7.41-7.38(m, 1H). FAB/MS(m/z): 296(M$^+$+1). |

EXAMPLE 4

Preparation of 4-phenylazophenyl aminobenzoxazole

2-Aminophenol (100 mg, 0.92 mmol) and 4-phenylazophenyl isothiocyanate (139 μl, 0.92 mmol) in methanol (25 ml) was stirred at room temperature for a day. The precipitate was filtered and washed with ether (5 ml) to obtain N-(2-hydroxyphenyl)-N'-4-phenylazophenyl thiourea as a white powder. N-(2-hydroxyphenyl)-N'-4-phenylazophenyl thiourea (100 mg, 0.41 mmol) was then treated with trifluoroacetic acid (5 ml), refluxed for a day, trifluoroacetic acid was removed by rotary evaporation, and the crude product was purified by column chromatography (ethyl acetate: hexane=3: 1 v/v) to obtain the title compound as a orange powder.

EXAMPLES 5 to 11

Various Benzoxazole compounds were obtained by the procedure of Example 4.

The compounds obtained in Examples 4 to 11 and characteristic properties thereof are shown in Table 2.

TABLE 2

| Ex. | $R^{1'}$ | $R^7$ | Data |
|---|---|---|---|
| 4 | —H | 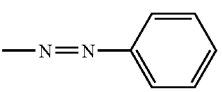 —N=N—⟨phenyl⟩ | mp: 209-210.5° C.<br>IR(KBr): 3384, 2922, 2852, 1664, 1460, 1019, cm$^{-1}$.<br>$^1$H NMR(acetone-d$_6$, 400MHz): δ9.97(s, NH), 8.12-8.10 (d, J=8Hz, 2H), 8.05-8.03(d, J=8Hz, 2H), 7.94-7.92 (d, J=8Hz, 2H), 7.61-7.57(t, J=12Hz, 2H), 7.55-7.51 (t, J=12Hz, 2H), 7.46-7.44(d, J=8Hz, 1H), 7.30-7.26 (t, J=12Hz, 1H), 7.21-7.17(t,J=12Hz, 1H). FAB/MS(m/z): 315(M$^+$+1). |
| 5 | —H | —H | mp: 180-182° C.<br>IR(KBr): 3385, 2922, 2852, 1664, 1460, 1019, 7.34, cm$^{-1}$.<br>$^1$H NMR(acetone-d$_6$, 400MHz): δ9.47(s, NH), 7.86-7.84 (d, J=8Hz, 2H), 7.43-7.41(d, J=8Hz, 1H), 7.39-7.35 (t, J=12Hz, 3H), 7.23-7.19(t, J=12Hz, 1H), 7.13-7.09 (t, J=12Hz, 1H), 7.06-7.02(t, J=12Hz, 1H). FAB/MS(m/z): 211(M$^+$+1). |

TABLE 2-continued

[Structure: R¹'-substituted benzoxazole with NH linker to R⁷-substituted phenyl]

| Ex. | R¹' | R⁷ | Data |
|---|---|---|---|
| 6 | —H | —C₂H₅ | mp: 123-125.3° C.<br>IR(KBr): 3207, 2965, 2928, 1530, 1191, 746, cm⁻¹.<br>¹H NMR(acetone-d₆, 400MHz): δ7.83-7.81(d, J=8Hz, 1H), 7.43-7.41(d, J=8Hz, 2H), 7.23-7.21(d, J=8Hz, 2H), 7.06-7.02(t, J=12Hz, 1H), 6.93-6.91(d, J=8Hz, 1H), 6.86-6.82(t, J=12Hz, 1H), 2.60(q, 2H), 1.19(t, 3H).<br>FAB/MS(m/z): 239(M⁺+1). |
| 7 | —Cl | —N=N—C₆H₅ | mp: 191-192.3° C.<br>IR(KBr): 3401, 2917, 2847, 1701, 1599, 1567, 1449, 1202, 1148, cm⁻¹.<br>¹H NMR(acetone-d₆, 400MHz): δ10.05(s, NH), 8.06-8.00 (q, 4H), 7.91-7.89(d, J=8Hz, 2H), 7.59-7.55(t, J=12Hz, 2H), 7.53-7.51(d, J=8Hz, 2H), 7.45-7.43(d, J=8Hz, 1H).<br>FAB/MS(m/z): 349(M⁺+1). |
| 8 | —Cl | —H | mp: 183-186.1° C.<br>IR(KBr): 3385, 2922, 2852, 1664, 1460, 1019, 734, cm⁻¹.<br>¹H NMR(acetone-d₆, 400MHz): δ9.6(s, NH), 7.83-7.81 (d, J=8Hz, 1H), 7.43-7.41(d, J=8Hz, 2H), 7.40-7.39(s, 1H), 7.38-7.36(d, J=8Hz, 1H), 7.30-7.29(s, 3H).<br>FAB/MS(m/z): 211(M⁺+1). |
| 9 | —Cl | —C₂H₅ | mp: 196-198° C.<br>IR(KBr): 3342, 2965, 2917, 1540, 1255, cm⁻¹.<br>¹H NMR(acetone-d₆, 400MHz): δ9.53(s, NH), 7.73-7.01 (d, J=8Hz, 2H), 7.40(s, 1H), 7.37-7.35(d, J=8Hz, 1H), 7.23-7.21(d, J=8Hz, 2H), 7.11-7.09(d, J=8Hz, 1H), 2.60(q, 2H), 1.20(q, 3H).<br>FAB/MS(m/z): 273(M⁺+1). |
| 10 | —NO₂ | —N=N—C₆H₅ | IR(KBr): 3342, 2922, 2847, 1600, 1573, cm⁻¹.<br>¹H NMR(acetone-d₆, 400MHz): δ10.24(s, NH), 8.31(s, 1H), 8.17-8.14(d, 1H), 8.09-8.06(d, 2H), 8.05-8.02(d, 2H), 7.93-7.90(d, 2H), 7.68-7.66(d, 1H), 7.59-7.55(t, 2H), 7.54-7.51(d, 1H).<br>FAB/MS(m/z): 359(M⁺). |
| 11 | —NO₂ | —C₂H₅ | mp: 161-163.5° C.<br>IR(KBr): 3325, 2922, 2847, 1578, 1519, cm⁻¹.<br>¹H NMR(acetone-d₆, 400MHz): 9.55(s, NH), 7.85-7.83 (d, J=8Hz, 1H), 7.44-7.42(d, J=8Hz, 2H), 7.25-7.23(d, J=8Hz, 2H), 6.73-6.71(d, J=8Hz, 1H), 2.60(q, 2H), 1.20(q, 3H).<br>FAB/MS(m/z): 284(M⁺+1). |

EXAMPLE 12

Preparation of 2-phenyl benzothiazole 1 g of 2-chlorotrytyl chloride resin (1.66 mmol/g, 1 eq) was allowed to swell in methylene chloride for 3-5 min, 1.162 mmol of N,N-diisopropylethylaminem (0.202 ml, 0.7 eq) and 1.66 mmol of aminothiophenol (0.178 ml, 1 eq) were added thereto, and the mixture was gently stirred for 3 hr at room temperature. Then, the resin was filtered and washed with a mixture of methylene chloride, methanol and N,N-diisopropylethylamine (85:10:5 v/v/v) to obtain 2-chlorotrityl resin loaded with 0.332 mmol/g of 2-aminobenzenethiol. The loaded 2-chlorotrityl resin 200 mg was suspended in 5-6 ml of N,N-dimethylformamide, 0.996 mmol of benzoyl chloride (0.116 ml, 3 eq) and the mmol of N,N-diisopropylethylamine (0.173 ml, 3 eq) were added thereto, and the mixture was shaken for 3 hr at room temperature. Then, the resin was filtered and washed with 5×10 ml N,N-dimethylformamide and 5×10 ml methylene chloride. The resin still remaining on the filter was then treated with 20 ml portions of 65% trifluoroacetic acid/methylene chloride and 5% triethylsilane/methylene chloride. The obtained filtrates were concentrated in a vacuum to obtain an oily residue, which was dissolved in 10 ml of N,N-dimethylformamide/methanol (9:1 v/v) containing 0.2 mmol of dithiothreitol (0.031 g). After 3 hr of standing at room temperature, the mixture was extracted with ether, washed with water, dried and concentrated in a vacuum to obtain the title compound as a white powder.

EXAMPLES 13 to 25

Various benzothiazole compounds were obtained by the procedure of Example 12.

The compounds obtained in Examples 12 to 25 and characteristic properties thereof are shown in Table 3.

TABLE 3

[Structure: benzothiazole-2-yl attached to a phenyl ring substituted with R⁵, R⁶, R⁷, R⁸]

| Ex. | R$^5$ | R$^6$ | R$^7$ | R$^8$ | Data |
|---|---|---|---|---|---|
| 12 | —H | —H | —H | —H | mp: 110-112° C.<br>$^1$H NMR(acetone-d$_6$, 400MHz): δ 8.17-8.13(t, J=12Hz, 2H), 8.11-3.09 (d, J=8Hz, 1H), 8.07-8.05(d, J=8Hz, 1H), 7.59-7.54(m, 4H), 7.49-7.45(t, J=12Hz, 1H).<br>FAB/MS(m/z): 212(M$^+$+1). |
| 13 | —H | —H | —F | —H | mp: 128-130.5° C.<br>$^1$H NMR(acetone-d$_6$, 400MHz); δ 8.22-8.18(t, J=12Hz, 2H), 8.10-8.08 (d, J=8Hz, 1H), 8.06-8.04(d, J=8Hz, 1H), 7.58-7.54(t, J=12Hz, 1H), 7.49-7.45 (t, J=12Hz, 1H), 7.38-7.34(t, J=12Hz, 2H).<br>FAB/MS(m/z): 230(M$^+$+1). |
| 14 | —H | —H | —NO$_2$ | —H | mp: 232-233.7° C.<br>$^1$H NMR(acetone-d$_6$, 400MHz): δ 8.42(s, 4H), 8.18-8.16(d, J=8Hz, 1H), 8.14-8.12(d, J=8Hz, 1H), 7.63-7.59 (t, J=12Hz, 1H), 7.55-7.51(t, J=12Hz, 1H).<br>FAB/MS(m/z): 242(M$^+$+1). |
| 15 | —SCHF$_2$ | —H | —H | —H | mp: 188~190° C.<br>$^1$H NMR(Acetone-d6)δ8.07(1H, s)8.00(1H, dd, J=0.8 and 8.0Hz) 7.94~7.90(2H, m)7.87(1H, J=0.8 and 8.0Hz)7.45(1H, dt, J=1.2 and 8.0 Hz). |
| 16 | —H | —H | —CN | —H | mp: 120~123° C.<br>$^1$H NMR(Acetone-d6)δ 8.08~8.19(2H, m)7.87~7.90(2H, m) 7.59(1H, dt, J=1.2 and 8.0Hz) 7.51(1H, dt, J=1.2 and 8.0Hz) 7.14~7.18(2H, m).<br>FAB/MS(m/z): 237(M$^+$+1). |
| 17 | —H | —H | —O(CH$_2$)$_3$CH$_3$ | —H | $^1$HNMR(Acetone-d6)δ 8.03~8.07(3H, m)7.50(1H, dt, J=1.2 and 8.4Hz)7.39(1H, dt, J=1.2 and 8.4Hz) 7.07~7.11(2H, m) 4.10(2H, t, J=6.4Hz)1.71~1.81(2H, m) 1.47~1.54(2H, m)0.97(3H, t, J=7.6Hz)<br>FAB/MS(m/z): 284(M$^+$+1). |
| 18 | —Cl | —H | —H | —NO$_2$ | mp: 190~193° C.<br>$^1$H NMR(Acetone-d6)δ 9.23(1H, d, J=2.8Hz)8.41(1H, dd, J=2.8 and 8.8Hz) 8.20~8.24(2H, m)8.00(1H, d, J=8.8Hz)7.67(1H, dt, J=1.2 and 7.2Hz)7.59(1H, dt, J=1.2 and 7.2Hz).<br>FAB/MS(m/z): 247(M$^+$+1). |
| 19 | —H | —H | —CH$_3$ | —NH$_2$ | $^1$H NMR(Acetone-d6)δ 8.30(1H, dd, J=0.8 and 8.0Hz) 7.97(1H, dd, J=0.8 and 8.0Hz) 7.48~7.52(2H, m)7.41(1H, dt, J=1.2 and 8.0Hz)7.30(1H, dd, J=1.6 and 7.6Hz)7.13(1H, d, J=7.6Hz).<br>FAB/MS(m/z): 241(M$^+$+1). |
| 20 | —H | —H | —CH$_3$ | —H | mp: 80~82° C.<br>$^1$H NMR(Acetone-d6)δ 8.07(1H, dd, J=0.8 and 8.4Hz) 8.00~8.05(3H, m)7.54(1H, dt, J=1.2 and 8.0Hz)7.44(1H, dt, J=1.2 and 8.0Hz)2.43(3H, s).<br>FAB/MS(m/z): 248(M$^+$+Na). |

TABLE 3-continued

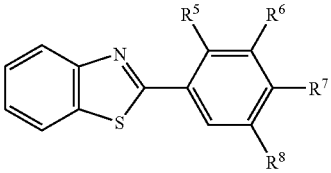

| Ex. | R⁵ | R⁶ | R⁷ | R⁸ | Data |
|---|---|---|---|---|---|
| 21 | —H | —OCH₃ | —OCH₃ | —H | mp: 132~133° C.<br>¹HNMR(Acetone-d6)δ<br>7.91(1H, brd, J=1.2 and 8.4Hz)<br>7.87(1H, brd, J=1.2 and 8.4Hz)7.40(1H, d, J=2.0Hz)<br>7.30(1H, dd, J=2.0 and 8.4Hz)<br>7.39(1H, dt, J=1.2 and 8.4Hz)<br>7.29(1H, dt, J=1.2 and 8.4Hz)<br>6.99(1H, d, J=8.4Hz)3.82(3H, s)3.78(3H, s).<br>FAB/MS(m/z): 272(M⁺+1). |
| 22 | —H | —CH₂Cl | —H | —H | ¹H NMR(Acetone-d6)δ<br>7.94(1H, brdJ=1.2 and 7.6Hz)<br>7.92~7.88(2H, m)7.41(1H, dt, J=1.2 and 8.0Hz)7.31(1H, dt, J=1.2 and 8.0Hz)<br>7.29~7.24(2H, m)2.30(2H, s).<br>FAB/MS(m/z): 260(M⁺+1). |
| 23 | | | | | ¹H NMR(Acetone-d6)δ<br>8.59(1H, dd, J=1.2 and 8.0Hz)<br>8.26(1H, dd, J=1.2 and 8.0Hz)<br>8.06~8.15(2H, m)7.58(1H, dt, J=1.2 and 8.4Hz)7.50(1H, dt, J=1.2 and 8.4)7.29(1H, d, J=8.0Hz).<br>FAB/MS(m/z): 273(M⁺+1). |
| 24 | | | | | ¹H NMR(Acetone-d6)δ<br>9.11(1H, d, J=2.4Hz)8.30(1H, dd, J=2.4 and 8.4Hz)8.17(1H, dd, J=1.2 and 8.0Hz)8.11(1H, dd, J=1.2 and 8.0Hz)7.86(1H, d, J=8.4Hz)7.61(1H, dt, J=1.2 and 8.4Hz)7.53(1H, dt, J=1.2 and 8.4Hz).<br>FAB/MS(m/z): 284(M⁺+1). |
| 25 | | | | | mp: 116~118° C.<br>1H NMR(Acetone-d6)δ<br>8.31~8.35(2H, m)8.21(1H, d, J=8.4Hz)8.15(1H, dd, J=0.8 and 8.0Hz)8.11(1H, dd, J=0.8 and 8.0Hz)7.97~8.00(2H, m)<br>7.94(1H, d, J=8.4Hz)7.61(1H, dt, J=1.2 and 8.0Hz)7.53(1H, dt, J=1.2 and 8.0Hz).<br>FAB/MS(m/z): 272(M⁺+1). |

TEST EXAMPLE

Measurement of 5-lipoxygenase Inhibition Activity

Bone marrow cells extracted from male BALB/cJ mice were cultured in a 1:1 (v/v) mixture of an enriched medium (RPMI 1640 medium containing penicillin 100 units/ml, streptomycin 100 mg/ml, gentamycin 10 mg/ml, 2 mM L-glutamate, 0.1 mM nonessential amino acids and 10% fetal bovine serum) and WEHI-3 cell conditioned medium as a source of interlukin-3 for 10 weeks. 4 weeks after the initiation of culture, over 98% of cells were confirmed as mast cells originated from bone marrow.

The obtained cells were suspended in the enriched medium to a concentration of $1 \times 10^6$ cells/ml. Then, a test compound prepared by dissolving each of the compounds of Examples 1 to 25 in dimethylsulfoxide (DMSO) was added therero to a concentration of 2.5 μg/ml, and the cells were cultured in a $CO_2$ incubator at 37° C. for 30 min. 100 ng/ml of stem cell factor (SCF) was added to the culture medium, and then, the culture was centrifuged at 120 xg for 20 min at 4° C. Then, the supernatant was separated and the amount of free $LTC_4$ was determined using an $LTC_4$ enzyme immunoassay kit (Cayman Chemical, Ann Arbor, Mich., U.S.A.). The stem cell factor (SCF) was recombinantly expressed by the baculovirus/insect cell expression system. After 20-min stimulation, the supernatants were isolated for further analysis by enzyme immunoassay.

$IC_{50}$ values, i.e., the concentrations of each test compound reducing the enzyme activity by 50% as compared the non-treated control, are shown in Table 4.

TABLE 4

| Example | IC$_{50}$(μM) |
| --- | --- |
| 1 | 9.52 |
| 2 | 10.27 |
| 3 | 1.58 |
| 4 | 6.28 |
| 5 | 8.91 |
| 6 | 1.21 |
| 7 | 12.61 |
| 8 | 4.50 |
| 9 | 0.95 |
| 10 | 28.37 |
| 11 | 23.88 |
| 12 | 7.26 |
| 13 | 11.22 |
| 14 | 11.04 |
| 15 | 1.54 |
| 16 | 4.32 |
| 17 | 9.30 |
| 18 | 2.50 |
| 19 | 4.16 |
| 20 | 5.27 |
| 21 | 2.76 |
| 22 | 2.49 |
| 23 | 6.11 |
| 24 | 5.55 |
| 25 | 2.92 |

As shown in Table 4, the compounds of formula (I) exhibited good 5-lipoxygenase inhibition activity. Therefore, the compounds of formula (I) can be advantageously used for preventing or treating a leukotriene-related disease such as asthma and inflammation diseases in a subject.

While the invention has been described with respect to the above specific embodiments, it should be recognized that various modifications and changes may be made to the invention by those skilled in the art which also fall within the scope of the invention as defined by the appended claims.

What is claimed is:

1. A method for inhibiting 5-lipoxygenase in a subject, comprising administering the compound of formula (I) or a pharmaceutically acceptable salt thereof to the subject in an amount effective for the inhibition of 5-lipoxygenase, wherein the compound of formula (I) is

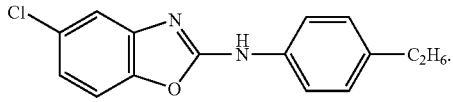

2. The method of claim 1, wherein said inhibition is used for treating a leukotriene-related disease selected from the group consisting of: asthma, pertussis, psoriasis, rheumatic arthritis, arthritis, inflammatory bowel disease, cystic fibrosis, acute/chronic bronchitis, sepsis, cardiac myoischemia, cardiac anaohvlaxis, ischemia and allergic rhinitis.

* * * * *